(12) United States Patent
Park et al.

(10) Patent No.: US 12,622,943 B2
(45) Date of Patent: May 12, 2026

(54) COMPOSITION FOR RELIEVING WOMAN MENOPAUSAL SYMPTOM COMPRISING A MIXED EXTRACT OF HOP AND CITRUS PEEL AND METHOD FOR TREATING OR ALLEVIATING MENOPAUSAL SYMPTOM USING THE SAME

(71) Applicant: LG HOUSEHOLD & HEALTH CARE LTD., Seoul (KR)

(72) Inventors: Dong-Jun Park, Seoul (KR); Eun-Mi Sun, Seoul (KR); Hong-Gu Lee, Seoul (KR); Ho-Song Cho, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 451 days.

(21) Appl. No.: 18/130,583

(22) Filed: Apr. 4, 2023

(65) Prior Publication Data

US 2023/0372426 A1     Nov. 23, 2023

(30) Foreign Application Priority Data

Apr. 4, 2022     (KR) ........................ 10-2022-0041720

(51) Int. Cl.
| | |
|---|---|
| *A61K 36/24* | (2006.01) |
| *A61K 9/00* | (2006.01) |
| *A61K 9/16* | (2006.01) |
| *A61K 31/352* | (2006.01) |
| *A61K 31/353* | (2006.01) |
| *A61K 31/573* | (2006.01) |
| *A61K 31/7048* | (2006.01) |
| *A61K 36/185* | (2006.01) |
| *A61K 36/488* | (2006.01) |
| *A61K 36/752* | (2006.01) |
| *A61P 3/06* | (2006.01) |
| *A61P 9/10* | (2006.01) |
| *A61P 9/12* | (2006.01) |
| *A61P 19/10* | (2006.01) |

(52) U.S. Cl.
CPC ............ *A61K 36/24* (2013.01); *A61K 9/0056* (2013.01); *A61K 9/1611* (2013.01); *A61K 9/1617* (2013.01); *A61K 9/1623* (2013.01); *A61K 9/1652* (2013.01); *A61K 9/1664* (2013.01); *A61K 31/352* (2013.01); *A61K 31/353* (2013.01); *A61K 31/573* (2013.01); *A61K 31/7048* (2013.01); *A61K 36/3486* (2024.05); *A61K 36/488* (2013.01); *A61K*
*36/752* (2013.01); *A61P 3/06* (2018.01); *A61P 9/10* (2018.01); *A61P 9/12* (2018.01); *A61P 19/10* (2018.01)

(58) Field of Classification Search
None
See application file for complete search history.

(56) References Cited

U.S. PATENT DOCUMENTS

| | | | | |
|---|---|---|---|---|
| 5,763,414 A | * | 6/1998 | Bok ........................ | A61P 43/00 |
| | | | | 514/456 |
| 2005/0032882 A1 | * | 2/2005 | Chen .................... | A61K 36/484 |
| | | | | 514/456 |
| 2007/0218155 A1 | | 9/2007 | Kuhrts | |
| 2021/0401918 A1 | | 12/2021 | Lee et al. | |

FOREIGN PATENT DOCUMENTS

| | | |
|---|---|---|
| EP | 1 543 834 A1 | 6/2005 |
| KR | 10-2017-0121532 A | 11/2017 |
| KR | 10-2020-0062036 A | 6/2020 |

OTHER PUBLICATIONS

Kim et al. Efficacy and safety of Kudzu flower—Mandarin peel on hot flashes and bone marjers in women during the menopausal transition: a randomized controlled trial. Nutrients, 12, 3237, pp. 1-13 (Year: 2020).*
Chiba, Hiroshige, et al. "Hesperidin, a citrus flavonoid, inhibits bone loss and decreases serum and hepatic lipids in ovariectomized mice." The Journal of nutrition 133.6: 1892-1897. (Year: 2003).*
Kim et al., "Inhibitory Effects of Compounds Isolated from Roots of Cynanchum Wilfordii on Oxidation and Glycation of Human Low-Density Lipoprotein (LDL)," Journal of Functional Foods, vol. 59, Jun. 5, 2019, pp. 281-290.
U.S. Office Action for U.S. Appl. No. 18/130,765, dated Aug. 13, 2025.
Wang et al., "Cynanchum Auriculatum Royle ex Wight., Cynanchum Bungei Decne. and Cynanchum Wilfordii (Maxim.) Hemsl.: Current Research and Prospects," Molecules, vol. 26, No. 23, Nov. 23, 2021, pp. 1-40 (41 pages total).

* cited by examiner

*Primary Examiner* — Bethany P Barham
(74) *Attorney, Agent, or Firm* — Birch, Stewart, Kolasch & Birch, LLP

(57) ABSTRACT

The present disclosure relates to a composition for treating or alleviating female menopausal symptoms, which contains a mixed extract of hop and citrus peel as an active ingredient, and a method for treating or alleviating menopausal symptoms. The composition of the present disclosure has superior effect of alleviating or treating female menopausal symptoms, particularly cardiovascular disease and/or osteoporosis.

10 Claims, No Drawings

COMPOSITION FOR RELIEVING WOMAN MENOPAUSAL SYMPTOM COMPRISING A MIXED EXTRACT OF HOP AND CITRUS PEEL AND METHOD FOR TREATING OR ALLEVIATING MENOPAUSAL SYMPTOM USING THE SAME

TECHNICAL FIELD

The present disclosure relates to a composition for alleviating female menopausal disorder and a method for treating or alleviating menopausal disorder using the same. More particularly, it relates to a composition comprising a mixed plant extract capable of alleviating various symptoms of female menopausal disorder, a use of the extract, and a method for treating or alleviating female menopausal disorder using the mixed extract.

BACKGROUND ART

Menopause is the time in women's lives when the reproductive function declines and ceases gradually. As women enter menopause, changes occur throughout the body including the vascular system, musculoskeletal system, genitourinary system and cranial nerves due to the imbalance and decrease in secretion of female hormones. That is to say, vasomotor symptoms and psychological symptoms are accompanied such as hot flushes, night sweats, sleep disorder, fatigue, depression, anxiety, inability to concentrate, memory disorder, dyspareunia due to urogenital atrophy, frequent urination, loss of skin elasticity due to collagen reduction, and breast sagging. It is also accompanied by various diseases such as dementia. Although menopausal symptoms differ from person to person, it has been reported that the quality of life of women worsens as more menopausal symptoms are experienced and as they are more severe and last longer. In addition, the menopausal symptoms are highly likely to develop into chronic diseases with physical aging.

In addition, during menopause, symptoms such as cold sweat, fatigue, nervousness, headache, sleep disorder (insomnia or early awakening), anxiety, apathy, dispiritedness, depression, muscle and joint pain, dizziness, etc. may appear. Among these symptoms, depression and anxiety are the most frequent symptoms experienced by modern people and have the greatest impact on the quality of life. Therefore, it is important to manage depression and anxiety well during menopause. In addition, it has been reported that the effect of estrogen on blood lipids, that is, problems with cholesterol content control, causes thromboembolism and hypertension and, in serious cases, can cause arteriosclerotic cardiovascular diseases.

During menopause, estrogen level is decreased, which is one of the factors that increase the risk of osteoporosis. Estrogen plays a role in promoting bone-forming cells and maintaining bone density. However, when estrogen level is decreased due to menopause, the secretion of nerve growth factor for maintaining bone tissue is decreased and, as a result, the strength of bone tissue is decreased and the risk of osteoporosis is increased. In addition, during menopause, the decreased in bone density can be accelerated further due to factors such as body weight increase, reduced physical activity, etc.

As the quality of life is improved gradually, the desire to manage the symptoms occurring during menopause and to spend a healthy menopausal period is increasing. Since hormone preparations widely used in existing medicines have immediate effects but have many side effects, interest in natural materials that can alleviate the female menopausal symptoms is increasing, and the need to study new physiological functions of various biological species is increasing gradually. In this regard, various preceding researches have been conducted, but researches on natural materials for alleviating female menopausal symptoms that contain ingredients that can be safely consumed by human as active ingredients and can improve the quality of life during menopause are still insufficient.

For treatment of menopausal symptoms, hormone therapy, drug therapy, exercise therapy and diet therapy can be applied. But, long-term use of female hormone therapy, which is widely used medically, can increase the risk of breast cancer, etc. and may increase the risk of uterine cancer, thrombotic vascular disease, gallbladder disease and hypertension. Therefore, in recent years, many researches have been conducted on phytoestrogens, which are reported to have functions similar to those of estrogen, to replace estrogen therapy and other drug therapies.

In many cases, the ingredients known to be effective in alleviating menopausal symptoms are effective for only one of the menopausal symptoms (e.g., hot flushes, osteoporosis, etc.). However, since more than one menopausal symptoms occur at the same time, it is important that complex effects are exhibited on various menopausal symptoms.

8-Prenylnaringenin, known as a functional ingredient of hop, is used in hormone replacement therapy for menopausal disorders. However, it is known that increased uterine weight and abnormal hormonal changes are observed when it is administered to animals at high doses. Accordingly, excessive use of hop may cause side effects.

Therefore, various researches are being conducted on methods that can be safely administered with few side effects while being effective for treating or alleviating menopause.

DISCLOSURE

Technical Problem

The present disclosure is designed to solve the problems of the related art, and therefore the present disclosure is directed to providing a novel composition for treating, preventing or alleviating female menopausal symptoms or a method for treating or alleviating female menopausal symptoms. In addition, the present disclosure is directed to providing a novel use of a mixed extract for treating, preventing or alleviating female menopausal symptoms.

Technical Solution

In an exemplary embodiment, the present disclosure provides a composition for treating or alleviating female menopausal symptoms, which contains a mixed extract of hop and citrus peel as an active ingredient. The composition contains 8-prenylnaringenin and hesperidin. Specifically, the composition contains 0.1-8 mg/g of 8-prenylnaringenin and 80-170 mg/g of hesperidin.

The mixed extract of hop and citrus peel may be contained in an amount effective for treating or alleviating female menopausal symptoms. For example, when the composition is formulated into a food, a medicine, etc., it may contain about 30-600 mg, about 30-550 mg, about 30-500 mg, about 30-450 mg, about 30-400 mg, about 30-350, about 30-300, about 30-250, about 30-200, about 30-150, about 30-120, about 30-100, about 30-60, about 30-50, about 50-600 mg, about 50-550 mg, about 50-500 mg, about 50-450 mg, about 50-400 mg, about 50-350, about 50-300, about 50-250, about 50-200, about 50-150, about 50-120, about 50-100, about 50-60, about 60-600 mg, about 60-550 mg, about 60-500 mg, about 60-450 mg, about 60-400 mg, about 60-350, about 60-300, about 60-250, about 60-200, about 60-150, about 60-120, about 60-100, about 100-600 mg, about 100-550 mg, about 100-500 mg, about 100-450 mg, about 100-400 mg, about 100-350, about 100-300, about 100-250, about 100-200, about 100-150, about 100-120, about 120-600 mg, about 120-550 mg, about 120-500 mg, about 120-450 mg, about 120-400 mg, about 120-350, about 120-300, about 120-250, about 120-200, about 120-150, about 150-600 mg, about 150-550 mg, about 150-500 mg, about 150-450 mg, about 150-400 mg, about 150-350, about 150-300, about 150-250, about 150-200, about 200-600 mg, about 200-550 mg, about 200-500 mg, about 200-450 mg, about 200-400 mg, about 200-350, about 200-300, about 200-250, about 250-600 mg, about 250-550 mg, about 250-500 mg, about 250-450 mg, about 250-400 mg, about 250-350, about 250-300, about 300-600 mg, about 300-550 mg, about 300-500 mg, about 300-450 mg, about 300-400 mg, about 300-350, about 350-600 mg, about 350-550 mg, about 350-500 mg, about 350-450 mg, about 350-400 mg, about 400-600 mg, about 400-550 mg, about 400-500 mg, about 400-450 mg, about 450-600 mg, about 450-550 mg, about 450-500 mg, about 500-600 mg, about 500-550 mg or about 550-600 mg, e.g., about 100 mg, about 120 mg, about 150 mg, about 180 mg, about 200 mg, about 240 mg, about 250 mg, about 300 mg, about 350 mg, about 360 mg, about 400 mg, about 420 mg or 600 mg of the mixed extract. The above amounts may be understood as daily, weekly or monthly doses, and may be understood as the amounts administered at once. The expression 'about' used herein may be understood as an error range of ±10% of the corresponding values. For example, about 100 mg may be understood as 90-110 mg. The mixed extract may be a mixture of a hop extract and a citrus peel extract at a weight ratio of 1:0.1-10.

In another exemplary embodiment, the composition may further contain an extract of *Pueraria* flower.

The mixed extract may contain hop, citrus peel and *Pueraria* flower at a weight ratio of 1:0.1-10:0.1-10.

The composition may contain 0.005-30 wt % of a hop extract, specifically 0.01-28 wt %, 0.05-25 wt %, 0.1-23 wt %, 0.5-22 wt %, 1-21 wt % or 5-20 wt % of a hop extract, based on the total weight of the composition. The composition may contain 0.005-30 wt % of a citrus peel extract, specifically 0.01-28 wt %, 0.05-25 wt %, 0.1-23 wt %, 0.5-22 wt %, 1-21 wt % or 5-20 wt % of a citrus peel extract, based on the total weight of the composition. The above content ranges may be advantageous for achieving the purpose of the present disclosure.

The female menopausal symptoms may include menopausal cardiovascular disease or osteoporosis. The composition may be provided as a pharmaceutical composition or a food composition, specifically a health functional food composition.

The composition may be provided as a composition for treating or alleviating female menopausal symptoms, which has estrogen receptor beta activity, osteoblast differentiation-promoting effect, bone component production-promoting effect, cholesterol synthase activity-inhibiting effect, and nitric oxide production-promoting effect.

In another exemplary embodiment, the present disclosure provides a method for treating or alleviating female menopausal symptoms by administering an effective amount of a mixed extract of hop and citrus peel to an individual in need of treatment or alleviation of female menopausal symptoms.

The mixed extract may further contain an extract of *Pueraria* flower.

The mixed extract may be a mixture of a hop extract and a citrus peel extract at a weight ratio of 1:0.1-10.

The mixed extract may be a mixture of a hop extract, a citrus peel extract and an *Pueraria* flower extract at a weight ratio of 1:0.1-10:0.1-10.

The method may include a step of administering a composition containing the mixed extract, and the composition may contain 5-20 wt % of a hop extract and 5-20 wt % of a citrus peel extract based on the total weight of the composition.

The female menopausal symptoms may include menopausal cardiovascular disease or osteoporosis.

The mixed extract used in the method for alleviation or treatment may contain 8-prenylnaringenin and hesperidin, and the mixed extract may contain 0.1-8 mg/g of 8-prenylnaringenin and 80-170 mg/g of hesperidin.

The present disclosure may provide a method for treating or alleviating female menopausal symptoms, which provides estrogen receptor beta activity, osteoblast differentiation-promoting effect, bone component production-promoting effect, cholesterol synthase activity-inhibiting effect and nitric oxide production-promoting effect.

Advantageous Effects

A composition containing a mixed extract according to the present disclosure is effective in alleviating female menopausal symptoms. In particular, since it is effective in preventing or alleviating cardiovascular disease and/or osteoporosis among the female menopausal symptoms, it can be usefully used in hormone replacement therapy (HRT) for preventing or alleviating menopausal symptoms.

In addition, since the composition containing a mixed extract according to the present disclosure has few side effects and is safe enough to be used as a food, unlike the existing treatments for female menopausal symptoms, it is highly useful as a treatment for cardiovascular disease and/or osteoporosis among female menopausal symptoms.

BEST MODE

In an exemplary embodiment, the present disclosure provides a composition for treating, preventing or alleviating female menopausal symptoms, which contains a mixed extract of hop and citrus peel as an active ingredient. In another exemplary embodiment, the present disclosure provides a use of the mixed extract or the composition for treating, preventing or alleviating female menopausal symptoms. In another exemplary embodiment, the present disclosure provides a method for treating, preventing or alleviating female menopausal symptoms, which includes administering an effective amount of a mixed extract of a hop extract and a citrus peel extract to an individual in need thereof.

The inventors of the present disclosure have researched on a mixed extract capable of providing superior effect of alleviating menopausal symptoms while using less hop than when a hop extract is used to have an effect of alleviating menopausal symptoms alone, and have completed the present disclosure. In particular, when the hop extract is used together with citrus peel, a superior effect of alleviating menopausal symptoms, specifically promotion of bone formation and improvement of blood lipids, can be achieved as compared to when it is used alone. Especially, the composition may provide an effect of alleviating menopausal cardiovascular disease and/or osteoporosis. In addition, the use of the mixed extract of hop and citrus peel and/or a mixed extract of hop, citrus peel and *Pueraria* flower (specifically *Pueraria thomsonii* flower) can avoid uterine enlargement symptoms, etc. which may occur when a large amount of hop is used to ameliorate the symptoms. Also, preference can be improved by using a smaller amount of hop.

In another exemplary embodiment, the composition may further contain another plant extract, specifically an extract of *Pueraria* flower and/or *Cynanchum wilfordii*. In another exemplary embodiment, the mixed extract may be an extract further containing *Pueraria thomsonii* flower and/or *Cynanchi wilfordii*.

The mixed extract of hop and citrus peel of the present disclosure may exhibit a better effect of alleviating female menopausal symptoms and fewer side effects when hop and citrus peel are used together. In particular, superior estrogen receptor beta activity, cardiovascular disease-reducing effect and osteoporosis-alleviating effect can be achieved. In addition, the effect of the mixed extract of the present disclosure may be improved further when it further contains *Pueraria* flower and/or *Cynanchum wilfordii*.

Hop (hops, *Humulus lupulus*) is a tendril plant native to Europe, Australia, North America, etc. Various compounds present in a hop extract are known to exhibit various physiological activities including anticancer, antioxidant and skin-whitening effects. Specifically, the mixed extract of the present disclosure may contain an extract obtained from the shoot, flower, bud or fruit of hop, more specifically an extract obtained from the flower or bud of hop. Compounds such as isoxanthohumols, etc. including 8-prenylnaringenin are known as active ingredients in the hop extract. However, hop has the problem that the administration dose is limited because the uterine weight of mice was increased when it was administered in excess amounts and it has characteristic odor and very strong astringent taste.

Citrus peel refers to the rind of the ripe fruit of tangerine (*Citrus unshiu* Markovich), mandarin orange (*Citrus reticulata* Blanco), their cultivated varieties or related plants in the same genus of the family Rutaceae.

*Pueraria* flower refers to the flower of kudzu, specifically the flower of *Pueraria thomsonii*.

*Cynanchum wilfordii* refers to the tuberous root of *Cynanchum wilfordii*.

The inventors of the present disclosure have completed the present disclosure by finding out that the mixed extract of hop and citrus peel exhibits superior effect of promoting estrogen beta receptor activity, inhibiting cholesterol synthesis, increasing NO production for vascular relaxation, promoting osteoblast differentiation and increasing the production of bone tissue components, and thus can exhibit an effect of alleviating, preventing and/or treating female menopausal symptoms, particularly menopausal cardiovascular disease and/or osteoporosis among them.

In the present disclosure, the 'menopausal symptoms' is a general term for symptoms and diseases that appear in women before and after menopause as the secretion of estrogen decreases due to the aging of ovaries, etc. It is also called 'menopausal syndrome' or 'climacteric symptoms'. The menopausal or climacteric symptoms may range from the symptoms that negatively affect the quality of life, such as hot flushes, sweating, nervousness, sleep disorder, etc., to the symptoms that may cause severe side effects such as cardiovascular disease, osteoporosis, etc. In particular, the mixed extract of the present disclosure may be advantageous in alleviating the symptoms such as cardiovascular disease, osteoporosis, etc.

In the present disclosure, the menopausal cardiovascular disease is understood to encompass not only the diseases directly caused by various causes such as ovarian dysfunction, disorder of the circulatory system, etc. but also the secondary diseases derived from the diseases. The menopausal cardiovascular disease may include hypertension, coronary artery disease, angina, myocardial infarction, stroke, arrhythmia, etc., although not being limited thereto.

In the present disclosure, osteoporosis refers to the condition in which the risk of fracture is high due to decreased bone strength, owing to genetic factors, premature menopause, medication, smoking, etc. Menopausal osteoporosis may occur due to decreased hormone production owing to menopause. The menopausal osteoporosis refers to the symptoms of osteoporosis caused by imbalance between osteoblasts involved in bone formation and osteoclasts involved in tissue destruction and resorption owing to decreased hormone production in postmenopausal women.

In the present disclosure, 'prevention' refers to any action of suppressing or delaying the symptoms by administering the mixed extract and/or composition of the present disclosure.

In the present disclosure, 'treatment' refers to any action of ameliorating or eliminating the symptoms by administering the mixed extract and/or composition of the present disclosure.

In the present disclosure, 'alleviation' refers to any action of ameliorating or favorably changing the symptoms by administering the mixed extract and/or composition of the present disclosure as compared to before the administration.

The extract contained in the composition of the present disclosure may be contained in an effective amount. The term 'effective amount' refers to an amount of the extract capable of suppressing or delaying menopausal symptoms, particularly cardiovascular disease and/or osteoporosis in women, or ameliorating the symptoms that have occurred already. In an exemplary embodiment, it may be understood as the amount administered orally to an individual, which is capable of suppressing, delaying, ameliorating, treating or alleviating menopausal symptoms. Those skilled in the art should be aware that the effective amount may vary from one individual to another depending on factors such as age, etc.

In the present disclosure, the 'mixed extract' refers to a mixture of two or more plant extracts, and may contain a mixture of two, three, four or more plant extracts. The mixed extract may be obtained by mixing two or more plant extracts or by mixing two or more plants and extracting the mixture.

The mixed extract may be provided into various ingestible forms, specifically a dry powder.

The content of the mixed extract contained in the composition is not specially limited. The mixed extract may be contained in various amounts as long as it can prevent, alleviate or treat menopausal symptoms or cardiovascular disease and/or osteoporosis. For example, the mixed extract of hop and citrus peel, or the mixed extract of hop, citrus peel and *Pueraria thomsonii* flower may be contained in an amount of 0.01-65 wt %, 0.1-60 wt %, 1-55 wt %, 10-52 wt %, 15-51 wt % or 20-50 wt % based on the total composition.

In another exemplary embodiment, the mixed extract may contain a mixture of a hop extract and a citrus peel extract at a weight ratio of 1:0.1-10, specifically 1:0.15-8, more specifically 1:0.5-5, further more specifically 1:1-3. In another exemplary embodiment, the mixed extract may contain a mixture of a hop extract, a citrus peel extract and an *Pueraria* flower extract at a weight ratio of 1:0.1-10:0.1-10, specifically 1:0.15-8:0.15-8, more specifically 1:0.5-5: 0.5-5, further more specifically 1:1-3:1-3. When the extracts are mixed within the above ranges, the effect of alleviating cardiovascular disease and/or osteoporosis may be superior. In addition, the astringent taste of hop may be reduced and preference may be improved.

In an exemplary embodiment of the present disclosure, the extract may be contained in an amount of 1-1000 mg, specifically 5-500 mg, based on 1 g of the composition. Specifically, the contents of all the ingredients used in the present disclosure do not exceed the maximum contents stated in the related laws and regulations of Korea, China, the Unites States, Europe, Japan, etc. (e.g., Regulations on the Safety Standards, etc. of Cosmetics (Korea), Safety and Technical Standards for Cosmetics (China), Food Code (Korea), Food Additives Code (Korea), Health Functional Food Code (Korea), Hygiene Standers (China), etc.). That is to say, the ingredients according to the present disclosure are contained in the cosmetic, food or personal care composition according to the present disclosure within the content limits permitted by the related laws, regulations and standards of each country.

In the present disclosure, the 'extract' may be prepared by extracting a plant, etc. with an extraction solvent or by conducting fractionation by adding a fractionation solvent to an extract prepared by extracting with the extraction solvent. The extract may be extracted by various methods such as hot water extraction, distillation extraction, solvent extraction, compression extraction, cold extraction, reflux cooling extraction, ultrasonic extraction, electrolytic extraction, supercritical extraction, etc., and may also be extracted using two or more extraction methods described above. A fraction obtained by fractionating the mixed extract of the present disclosure may also be included in the scope of the present disclosure.

The extract or fraction includes the extract itself and all forms of extracts that can be obtained from the extract, including a dried product obtained by diluting or concentrating the extract and then drying the same, a crude product or purified product of the extract, a mixture thereof, etc. Specifically, the extract of the present disclosure may be prepared into a dry powder after extraction. In addition, after performing extraction or fractionation, the extract may be concentrated or the solvent may be removed by filtration under reduced pressure and additional concentration and/or freeze-drying. The obtained extract may be stored in a deep freezer until use.

The extraction solvent is not specially limited and any solvent known in the art may be used as long as the extract exhibiting the effect desired by the present disclosure can be achieved. Specifically, one or more selected from a group consisting of water and an organic solvent may be used. One or more solvent selected from a group consisting of a C1-5 alcohol such as methanol, ethanol, etc., ethyl acetate, acetone and chloroform may be used as the organic solvent. Specifically, water, ethanol or a mixture thereof may be used. Specifically, 35-95% ethanol, more specifically 60-90% ethanol, may be used as the ethanol.

In addition, the term 'extract' used in the present specification means a crude extract as described above but also includes a fraction obtained by additionally fractionating the extract in a broad sense. That is to say, it includes not only an extract obtained by squeezing or extracting a raw material with the extraction solvent described above but also a product obtained by further purifying the same. For example, a fraction obtained by passing the extract through an ultrafiltration membrane having a certain molecular weight cut-off value and fractions obtained by various additional purification methods such as chromatography (designed for separation according to size, charge, hydrophobicity or affinity) are included in the extract of the present disclosure.

In addition, the mixed extract of the present disclosure may pass through an additional process, e.g., removal of the solvent through filtration, concentration or drying, or all of filtration, concentration and drying. For example, the filtration may be performed using filter paper or a vacuum filter, the concentration may be performed using a vacuum concentrator, and the drying may be performed by spray drying, freeze-drying, etc. to obtain the mixed extract in the form of a powder.

In the mixed extract of the present disclosure, the hop extract may be obtained by extracting hop with ethanol after supercritical extraction and then preparing the same into a powder, and the citrus peel extract may be obtained by extracting citrus peel with hot water and then preparing the same into a powder. For example, the hop extract may be obtained by extracting hop with 50-80% ethanol after supercritical extraction using carbon dioxide or the hop extract may be purchased from Naturex (France). Specifically, in a method for preparing the mixed extract according to an exemplary embodiment of the present disclosure, the extraction method may not be specially limited as long as the hop extract can contain 0.1-8 mg, specifically 0.5-5 mg, more specifically 1-4 mg, of 8-prenylnaringenin per 1 g of the extract. In addition, the extraction method may not be specially limited as long as the citrus peel extract can contain 80-170 mg, specifically 85-160 mg, more specifically 90-150 mg, of hesperidin per 1 g of the extract. When extracted by the extraction method described above, the mixed extract may exhibit superior effect of alleviating menopausal symptoms, particularly the effect of treating osteoporosis and/or cardiovascular disease.

In a specific example, when the degree of alleviation of menopausal symptoms was investigated using the mixed extract, it was confirmed that estrogen receptor activity was improved in cells treated with the mixed extract and menopausal symptoms was alleviated in a test group which ingested the mixed extract of the present disclosure.

In another exemplary embodiment, the fractionation solvent may be water, butanol, ethyl acetate, chloroform, hexane or a mixture thereof. The fraction may be obtained by fractionating an extract, specifically a crude extract, prepared by the extraction method described above. The fractionation solvent may be a solvent selected from a group consisting of ethyl acetate, ether, chloroform, benzene, hexane, methylene chloride and a mixed solvent thereof. Specifically, it may be hexane. Specifically, the fractionation may be performed by sequentially adding hexane, chloroform, ethyl acetate, butanol and water to a crude extract and then sequentially obtaining a hexane fraction, a chloroform fraction, an ethyl acetate fraction, a butanol fraction and a water fraction.

In the present disclosure, the method for preparing the extract or the mixed extract is not limited specially and methods commonly used in the art may be employed. Non-limiting examples of the extraction method include hot water extraction, ultrasonic extraction, filtration, reflux extraction, etc., and these may be performed alone or in combination. In addition, the extract may be extracted further one or more times in the same manner to obtain a high-purity extract.

The present disclosure may provide a composition for preventing or alleviating female menopausal symptoms, which contains the mixed extract as an active ingredient. Specifically, the composition may be provided in the form of cosmetics, pharmaceuticals, foods or quasi-drugs. Particularly, it may be provided as specifically a health functional food or a medicine.

The pharmaceutical composition according to the present disclosure may contain a pharmaceutically effective amount of the mixed extract either alone or in combination with one or more pharmaceutically acceptable carrier or additive. The "pharmaceutically acceptable" means that the composition is physiologically acceptable and nontoxic when administered to human, without inhibiting the action of the active ingredient or causing allergic reactions such as gastrointestinal disorders and dizziness or similar reactions. The type of the carrier that may be used in the present disclosure is not specially limited, and any pharmaceutically acceptable carrier commonly used in the art may be used. Non-limiting examples of the carrier include saline, sterile water, Ringer's solution, buffered saline, albumin injection solution, dextrose solution, maltodextrin solution, glycerol, ethanol, etc. These may be used either alone or in combination. Examples of the additive include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, methyl hydroxybenzoate, propyl hydroxybenzoate, talc, magnesium stearate, mineral oil, etc. In addition, the pharmaceutical composition may further contain a filler, an anti-coagulant, a lubricant, a wetting agent, a flavoring agent, an emulsifier, an antiseptic, etc.

The "pharmaceutically effective amount" refers to an amount which exhibits a greater response than that of a negative control group, and specifically refers to an amount which is sufficient to exhibit the effect of preventing, alleviating and/or treating menopausal disorder.

In addition, the pharmaceutical composition of the present disclosure may be formulated by a method known in the art to provide rapid, sustained or delayed release of the active ingredient after administration to a mammal. The formulation may be in the form of a powder, a granule, a tablet, an emulsion, a syrup, an aerosol, a soft or hard gelatin capsule, a sterilized injectable solution or a sterile powder.

The pharmaceutical composition of the present disclosure may be administered orally or parenterally although the administration route is not limited thereto. The parenteral administration route may include various routes such as transdermal, intranasal, intraperitoneal, intramuscular, subcutaneous or intravenous routes.

In addition, the pharmaceutical composition of the present disclosure may be administered with in combination with a known compound having the effect of preventing, alleviating and/or treating menopausal disorder.

In another exemplary embodiment, the present disclosure provides a food composition.

The food composition of the present disclosure includes all processed forms of natural materials such as a food, a functional food, a nutritional supplement, a health food, a food additive, etc. The food composition can be prepared into various forms according to common methods known in the art. For example, as a health food, the composition of the present disclosure itself may be prepared into a tea, a juice or a drink for drinking, or may be granulated, encapsulated or powdered for ingestion.

The type of the food is not specially limited and may include any food in the conventional sense. Non-limiting examples of the food to which the composition can be added include meat, sausage, bread, chocolate, candy, snack, confectionery, pizza, ramen, other noodles, gum, dairy products including ice cream, soup, beverages, tea, drinks, alcoholic beverages, vitamin complexes, etc. When the composition is used as a food additive, the composition may be added as it is or may be used together with other foods or food ingredients, and may be used appropriately according to common methods. In addition, the food composition of the present disclosure may further contain another active ingredient and/or additive that can be commonly used in a food composition. The food composition may contain a sitologically acceptable carrier. For example, the food composition according to the present disclosure may contain water-soluble vitamins such as thiamine (vitamin $B_1$), riboflavin, ascorbic acid, niacin and vitamin B6, fatty acids such as myristic acid, palmitic acid, stearic acid, oleic acid, linoleic acid, etc., a weak acid such as glycolic acid and acetic acid, and amino acids such as 8 essential amino acids, threonine, valine, methionine, isoleucine, leucine, phenylalanine, tryptophan and lysine, and aspartic acid, serine, glutamic acid, proline, glycine, alanine, cysteine, tyrosine, histidine, arginine, etc.

Specifically, the food composition of the present disclosure may be obtained by mixing the mixed extract with crystalline cellulose, lactose, seaweed powder, hydroxypropylmethyl cellulose, crosslinked sodium carboxymethyl cellulose, silicon dioxide, magnesium stearate, etc.

In another exemplary embodiment, the present disclosure provides a cosmetic composition containing any of the compositions described above.

The cosmetic composition of the present disclosure contains, in addition to the active ingredient of the present disclosure, ingredients commonly used in cosmetic compositions, e.g., a common adjuvant such as an antioxidant, a stabilizer, a solubilizer, a vitamin, a pigment and a fragrance and a carrier.

The cosmetic composition according to the present disclosure may be prepared into any formulation commonly used in the art. For example, it may be formulated into a solution, suspension, an emulsion, a paste, a gel, a cream, a lotion, a powder, a soap, a surfactant-containing cleanser, an oil, a powder foundation, an emulsion foundation, a wax foundation, a spray, etc., although not being limited thereto.

More specifically, it may be formulated into a softening lotion, a nourishing lotion, a nourishing cream, a massage cream, an essence, an eye cream, a cleansing cream, a cleansing foam, a cleansing water, a pack, a spray or a powder.

When the formulation of the present disclosure is a solution or an emulsion, a solvent, a solubilizer or an emulsifier may be used as a carrier ingredient, such as water, ethanol, isopropanol, ethyl carbonate, ethyl acetate, benzyl alcohol, benzyl benzoate, propylene glycol, 1,3-butylene glycol oil, fatty acid esters of glycerol, or fatty acid esters of polyethylene glycol or sorbitan.

When the formulation of the present disclosure is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier ingredient.

When the formulation of the present disclosure is a surfactant-containing cleanser, an aliphatic alcohol sulfate, an aliphatic alcohol ether sulfate, sulfosuccinic acid monoester, isethionate, an imidazolinium derivative, methyl taurate, sarcosinate, a fatty acid amide ether sulfate, an alkylamidobetaine, an aliphatic alcohol, a fatty acid glyceride, a fatty acid diethanolamide, a vegetable oil, a lanolin derivative, an ethoxylated glycerol fatty acid ester, etc. may be used as a carrier ingredient.

When the formulation of the present disclosure is a powder or a spray, lactose, talc, silica, aluminum metahydroxide, calcium silicate, polyamide powder, etc. may be used as a carrier ingredient. Especially, a spray may further contain a propellant such as chlorofluorohydrocarbon, propane/butane or dimethyl ether.

When the formulation of the present disclosure is a paste, a cream or a gel, an animal oil, a vegetable oil, a wax, paraffin, starch, tragacanth, a cellulose derivative, polyethylene glycol, silicone, bentonite, silica, talc, zinc oxide, etc. may be used as a carrier ingredient.

In another exemplary embodiment, the present disclosure provides a method for preventing or treating female menopausal symptoms or a method for preventing or treating osteoporosis and/or cardiovascular disease, which includes a step of administering an effective amount of the mixed extract or a composition containing the mixed extract to an individual who has female menopausal symptoms or suffers from or has the risk of osteoporosis and/or cardiovascular disease. In the present disclosure, the term "individual" refers to all animals including human, such as rat, mouse, livestock, etc., that suffer from or have the risk of female menopausal symptoms, more specifically osteoporosis and/ or menopausal cardiovascular disease. As a specific example, it may be a mammal including human. The composition of the present disclosure may be administered with a daily dose of 0.0001-100 mg/body weight kg, more specifically 0.001-100 mg/body weight kg, based on solid content. The recommended administration dose may be administered once a day or in several divided doses.

The mixed extract may further contain an extract of *Pueraria* flower.

The mixed extract may be a mixture of hop, citrus peel and *Pueraria* flower extracts at a weight ratio of 1:0.1-10:0.1-10.

The method may include a step of administering a composition containing the mixed extract, and the composition may contain 5-20 wt % of a hop extract and 5-20 wt % of a citrus peel extract based on the total weight of the composition.

The female menopausal symptoms may include menopausal cardiovascular disease or osteoporosis.

The mixed extract used in the method for alleviation or treatment contains 8-prenylnaringenin and hesperidin. The mixed extract may contain 0.1-8 mg/g of 8-prenylnaringenin and 80-170 mg/g of hesperidin.

The method for treating or alleviating female menopausal symptoms may provide estrogen receptor beta activity, osteoblast differentiation-promoting effect, bone component production-promoting effect, cholesterol synthase activity-inhibiting effect, and nitric oxide production-promoting effect.

In another exemplary embodiment, the present disclosure provides a use of the composition containing the mixed extract for preparation of a food or a therapeutic agent for alleviating, treating, preventing or ameliorating menopausal symptoms.

Hereinafter, examples, etc. will be described in detail to held understanding the present disclosure. However, the examples according to the present disclosure may be changed into various different forms, and the scope of the present disclosure should not be construed as being limited by the examples. The examples of the present disclosure are provided to more completely explain the present disclosure to those having ordinary knowledge in the art to which the present disclosure belongs. In the present specification, % may be understood to mean wt % unless specified otherwise.

<Preparation of Mixed Extract>

1. Preparation of Hop Extract

Hop was extracted using the flower of *Humulus lupulus* L by supercritical and ethanol extraction. Then, the extract was pulverized after passing through concentration, alkalinization, neutralization, separation and drying.

A hop extract containing 2-3 mg/g of 8-prenylnaringenin was prepared.

2. Preparation of Citrus Peel Extract

Citrus peel was treated enzymatically after hot water extraction of the peel of fruit of *Citrus unshiu* S. Markov or *Citrus reticulata* Blanco. Then, the extract was spray-dried after passing through cooling, filtration, centrifugation and sterilization.

A citrus peel extract containing 95-143 mg/g of hesperidin was prepared.

3. Preparation of *Pueraria thomsonii* Flower Extract

*Pueraria thomsonii* flower was extracted using the flower of *Pueraria thomsonii* Benth by ethanol extraction. Then, the extract was spray-dried after passing through filtration, concentration and sterilization.

Experimental Example 1. Evaluation of Estrogen Receptor Beta Activity

Evaluation was performed using a human ERβ reporter assay system (INDIGO Biosciences, IB300411-32). Experiment was conducted according to the manufacturer's protocol. After treating cells with samples of different concentrations and estrogen receptor beta on a 96-well plate for 24 hours, the solution was removed and 100 μL of a luciferase detection solution (included in the kit) was added. Luminescence was measured after leaving at room temperature for 5 minutes. The luminescence was measured with a microplate reader (Biotek, Synergy H1MF, luminescence mode) with measurement time set to 500 ms. The result is shown in Table 1. The treatment with the mixed extract of the hop extract and the citrus peel extract and together with the *Pueraria thomsonii* flower extract resulted in increased receptor activity even though the content of hop was decreased.

Experimental Example 2. Evaluation of Osteoblast Differentiation-Promoting Effect In order to investigate osteoblast differentiation-promoting effect, the activity of ALP (alkaline phosphatase), which is an osteoblast differentiation marker, in human osteoblast-like Saos-2 cells was measured. A uniform number of Saos-2 cells were cultured in a 24-well plate using a RPMI1640 medium supplemented with 10% FBS. After culturing for 24 hours, the medium was replaced with a phenol red-free RPMI1640 containing 2% charcoal-stripped FBS and the cells were cultured further for 3 days after treating with samples at different concentrations. Subsequently, ALP activity was measured with an alkaline phosphatase assay kit (Abcam, ab83369). Specifically, 200 μL of the cell culture was collected and centrifuged at 1000 rpm for 3 minutes. After putting 20 μL of the medium in the upper layer and 50 μL of a pNPP substrate into a 96-well plate and conducting reaction for 30 minutes, absorbance was measured at 405 nm. The result is shown in Table 1. It can be seen that when the mixed extract was used and, furthermore, when the *Pueraria thomsonii* flower extract was used together, the differentiation into osteoblasts was facilitated as compared to when the hop was used alone.

Experimental Example 3. Evaluation of Bone Component (Osteocalcin) Production-Promoting Effect In order to investigate osteogenesis-promoting effect, a uniform number of Saos-2 cells were cultured in a 24-well plate using a RPMI1640 medium supplemented with 10% FBS. After culturing for 24 hours, the medium was replaced with a phenol red-free RPMI1640 containing 10 mM β-glycerophosphate, 10 nM dexamethasone and 2% charcoal-stripped FBS and the cells were cultured further for 3 days after treating with samples at different concentrations. Subsequently, after changing the medium and treating with the samples in the same way, the cells were cultured further for 4 days. After culturing for a total of 7 days, 200 μL of the cell culture was collected and centrifuged at 1000 rpm for 3 minutes. Osteocalcin in the medium in the upper layer was quantified using a human osteocalcin DuoSet ELISA kit (R&D Systems, DY1419) according to the manufacturer's protocol. The result is shown in Table 1. It can be seen that when the mixed extract was used and, furthermore, when the *Pueraria thomsonii* flower extract was used together, the bone component production was facilitated as compared to when the hop was used alone.

Experimental Example 4. Evaluation of Inhibition of Cholesterol Synthase HMG-CoA Reductase Activity The effect of inhibiting the activity of HMG-CoA reductase, which is a rate-limiting enzyme in cholesterol synthesis, was investigated using an HMG-CoA reductase activity assay kit (Abcam, AB204701). The activity of HMG-CoA reductase was measured according to the manufacturer's protocol. The result is shown in Table 1. It can be seen that when the mixed extract was used and, furthermore, when the *Pueraria thomsonii* flower extract was used together, the activity of the cholesterol synthase was inhibited more than when the hop was used alone. Through this, it can be seen that the mixed extract has excellent effect of improving blood lipids.

Experimental Example 5. Evaluation of Promotion of Production of Blood Vessel-Relaxing Nitric Oxide (NO)

Nitric oxide (NO) is a signaling molecule involved in various physiological activities such as immunity, vasodilation, signaling, etc. In particular, it induces and stimulates various activities in the body. It dilates blood vessels and lowers blood pressure to a normal level by inducing the production of cGMP (cyclic guanosine monophosphate) and improves the flow of blood supplied to organs. In addition, it is effective in preventing stroke and, especially, heart attack such as myocardial infarction, etc. by preventing blood clots from adhering to blood vessels in the cardiovascular system.

In order to investigate the NO production-promoting effect of the samples, human umbilical vein endothelial cells (HUVECs) were inoculated to a 24-well plate (Falcon, 353047) with 1×10$^5$ cells per well and cultured for 24 hours using an EGM-2 medium (Lonza, CC-3162 containing an appropriate amount of FBS (fetal bovine serum) and P/S antibiotics (penicillin and streptomycin) under the condition of 5% $CO_2$ and 37° C., until about 80% more of the cells were adhered to the bottom of the well. Subsequently, after treating with the sample of each concentration, the cells were cultured further for 24 hours. After the culturing was completed, the concentration of NO in the medium was measured using a Griess reagent (Sigma, G4410). Specifically, 100 μL of the medium was mixed with 100 μL of the Griess reagent and measurement was made at a wavelength of 540 nm using a UV spectrophotometer (Biotek, Synergy H1MF). The result is shown in Table 1. It can be seen that when the mixed extract was used and, furthermore, when the *Pueraria thomsonii* flower extract was used together, the production of NO was increased as compared to when the hop was used alone. Through this, it can be seen that the mixed extract has excellent effect of improving blood flow by dilating blood vessels and preventing stroke and, especially, heart attack such as myocardial infarction, etc. by preventing blood clotting in the cardiovascular system.

The results of Test Examples 1-5 are summarized in the following table. The results are expressed as % improvement with respect to an untreated control group.

TABLE 1

|  |  | Estrogen beta | Cardiovascular markers | | Osteoporosis markers | |
| --- | --- | --- | --- | --- | --- | --- |
| Samples | Conc. | receptor activity-promoting effect (%) | Inhibition of cholesterol synthase activity (%) | Promotion of production of blood vessel-relaxing NO (%) | Promotion of differentiation of osteoblasts (%) | Production of bone tissue components (%) |
| Hop | 5 ppm | 16.78 | 17.80 | 16.35 | 12.52 | 11.99 |
|  | 10 ppm | 24.16 | 18.11 | 19.11 | 13.64 | 13.10 |
| Citrus peel | 5 ppm | 8.03 | 1.95 | 2.23 | 7.51 | 6.61 |
|  | 10 ppm | 12.01 | 3.81 | 3.07 | 8.12 | 8.46 |
| Hop + citrus peel | 5 ppm | 38.11 | 20.87 | 21.46 | 23.62 | 22.13 |
| (1:1 mixture) | 10 ppm | 52.98 | 23.66 | 22.52 | 27.40 | 28.59 |
| *Pueraria thomsonii* | 5 ppm | 24.23 | 5.71 | 7.66 | 2.49 | 1.94 |
| flower | 10 ppm | 36.98 | 8.43 | 8.65 | 2.87 | 2.48 |
| Hop + citrus peel + | 5 ppm | 114.31 | 28.02 | 29.73 | 29.47 | 29.42 |
| *Pueraria thomsonii* flower (1:1:1 mixture) | 10 ppm | 159.19 | 34.37 | 34.24 | 35.79 | 33.63 |

(n = 3)

<Sensory Evaluation>

Sensory evaluation was conducted by 20 trained subjects. They were asked to ingest the powders prepared according to the mixing ratios shown in Table 2 at a dose of 500 mg per each intake. The evaluation items consisted of a total of four items: 1) bitter taste felt immediately after the intake, 2) bitter aftertaste felt 5 minutes after the intake, 3) preference for flavor felt during the intake, and 4) overall preference. Each item was evaluated on a 9-point scale. For the bitter taste and the bitter aftertaste, a higher score means stronger bitterness. For the flavor and overall preference, a higher score means higher preference. The result is shown in Table 3.

TABLE 2

|  |  | Mixing ratio (%) | |
| --- | --- | --- | --- |
|  | Samples | Comparative Example | Example |
| | Hop | 36 | 18 |
| | Citrus peel | — | 18 |
| Food | Crystalline cellulose | 18 | |
| additives | Lactose | 20 | |
| | Seaweed powder | 20 | |
| | HPMC | 1 | |
| | Crosslinked CMC-Na | 3 | |
| | Silicon dioxide | 1 | |
| | Magnesium stearate | 1 | |

TABLE 3

|  | Sensory scores | | | |
| --- | --- | --- | --- | --- |
| Test groups | Bitter taste | Bitter aftertaste | Preference for flavor | Overall preference |
| Hop (Comparative Example) | 7.9 | 7.1 | 3.8 | 2.1 |
| Hop + citrus peel (Example) | 6.1 | 5.9 | 5.1 | 5.0 |

When the hop was used alone, the bitter taste was strong and the preference was low.

When the mixed extract of hop and citrus peel was used, the preference for taste and flavor was increased in addition to the improved effect of alleviating menopausal symptoms as compared to when the hop was used alone.

What is claimed is:

1. A method for treating or alleviating female menopausal symptoms, comprising a step of administering an effective amount of a mixed extract of hop, citrus peel, and Pueraria flower to an individual in need of treatment or alleviation of female menopausal symptoms, wherein the mixed extract comprises hop, citrus peel and Pueraria flower are at a weight ratio of 1:0.1-10:0.1-10.

2. The method for treating or alleviating female menopausal symptoms according to claim 1, wherein the method comprises a step of administering a composition comprising the mixed extract, and the composition comprises 5-20 wt % of a hop extract and 5- 20 wt % of a citrus peel extract based on the total weight of the composition.

3. The method for treating or alleviating female menopausal symptoms according to claim 1, wherein the female menopausal symptoms comprise at least one of menopausal cardiovascular disease or osteoporosis.

4. The method for treating or alleviating female menopausal symptoms according to claim 1, wherein the mixed extract comprises 8-prenylnaringenin and hesperidin, and the mixed extract comprises 0.1-8 mg/g of 8-prenylnaringenin and 80-170 mg/g of hesperidin.

5. The method for treating or alleviating female menopausal symptoms according to claim 1, wherein the method provides estrogen receptor beta activity, osteoblast differentiation-promoting effect, bone component production-promoting effect, cholesterol synthase activity-inhibiting effect, and nitric oxide production-promoting effect.

6. The method for treating or alleviating female menopausal symptoms according to claim 1, wherein the mixed extract comprises hop, citrus peel and Pueraria flower at a weight ratio of 1:0.15-8:0.15-8.

7. The method for treating or alleviating female menopausal symptoms according to claim 1, wherein the mixed extract comprises hop, citrus peel and Pueraria flower at a weight ratio of 1:0.5-5:0.5-5.

8. The method for treating or alleviating female menopausal symptoms according to claim 1, wherein the mixed extract comprises hop, citrus peel and Pueraria flower at a weight ratio of 1:1-3:1-3.

9. The method for treating or alleviating female menopausal symptoms according to claim 1, the mixed extract of hop, citrus peel and Pueraria thomsonii flower is contained in an amount of 0.01-65 wt % based on the total composition.

10. The method for treating or alleviating female menopausal symptoms according to claim 1, the mixed extract of hop, citrus peel and Pueraria thomsonii flower is contained in an amount of 10-52 wt % based on the total composition.

* * * * *